United States Patent [19]
Berghaus

[11] Patent Number: 5,258,027
[45] Date of Patent: Nov. 2, 1993

[54] TRACHREAL PROSTHESIS

[75] Inventor: Alexander Berghaus, Berlin, Fed. Rep. of Germany

[73] Assignee: Willy Rusch AG, Fed. Rep. of Germany

[21] Appl. No.: 997,102

[22] Filed: Dec. 21, 1992

Related U.S. Application Data

[63] Continuation of Ser. No. 645,226, Jan. 24, 1991, abandoned.

[51] Int. Cl.⁵ .............. A61F 2/20; A61F 2/02; A61F 2/04
[52] U.S. Cl. .............................. 623/9; 623/11; 623/12
[58] Field of Search ............... 623/11, 66; 128/200.26, 128/207.14, 207.15

[56] References Cited

U.S. PATENT DOCUMENTS

| | | | |
|---|---|---|---|
| 3,137,299 | 6/1964 | Tabor | 623/9 |
| 3,588,920 | 9/1969 | Wesolowski | 623/1 |
| 3,818,515 | 6/1974 | Neville | 623/9 |
| 4,041,931 | 8/1977 | Elliott et al. | 623/1 X |
| 4,140,126 | 2/1979 | Choudhury | 623/1 X |
| 4,562,596 | 1/1986 | Kornberg | 623/1 |
| 4,728,328 | 5/1988 | Hughes et al. | 623/12 |
| 4,747,849 | 5/1988 | Galtier | 623/12 |
| 4,795,465 | 1/1989 | Marten | 623/9 |
| 4,994,298 | 2/1991 | Yasuda | 623/12 X |
| 5,085,632 | 2/1992 | Ikada et al. | 604/29 X |

FOREIGN PATENT DOCUMENTS 8800813  2/1988  PCT Int'l Appl. ............... 623/1

*Primary Examiner*—Randall L. Green
*Assistant Examiner*—Dinh X. Nguyen
*Attorney, Agent, or Firm*—Walter A. Hackler

[57] ABSTRACT

The tracheal prosthesis is intended to replace damaged, diseased or missing tracheal and/or bronchial segments. The tracheal prosthesis comprises a plastic shaft which is embraced by hoops. The hoops 9 stabilize the thin film-like material wall. As in the case of the human trachea, the hoops leave an area of the plastic shaft uncovered so that a particularly resilient circumferential surface is obtained between the hoops, resembling the membranaceous part of the human trachea. The ends of the tracheal prosthesis are reinforced by spring elements. These spring elements ensure that the tracheal prosthesis is retained safely in the natural tracheal and/or bronchial stumps. The inner surface of the tracheal prosthesis is hydrophilized.

13 Claims, 4 Drawing Sheets

TRACHREAL PROSTHESIS

This is a continuation of Copending Application Ser. No. 07/645,226 filed on Jan. 24, 1991, now abandoned.

BACKGROUND OF THE INVENTION

The present invention relates to a tracheal prosthesis intended to replace damaged, diseased or missing tracheal and/or bronchial segments, comprising a plastic shaft provided with a lumen and arranged for having its free ends connected with the tracheal stumps to be joined.

A tracheal prosthesis of this type has been known under the name "Neville Prosthesis".

The use of an artificial trachea is indicated in all cases where extensive damage is found on a trachea, caused for example by accidents, destructive tissue growth and, this occurs particularly frequently, by indwelling respiration hoses if patients have to be treated in intensive-care units for extended periods of time. Given the fact that the trachea is an azygous organ, its proper function is of critical importance for the human organism. Damage caused to the mucosa during long-term artificial respiration frequently leads to subsequent cicatricial constrictions or even complete cicatricial occlusion of the trachea. Moreover, the growth of a cancer may result in occlusion, and accidents may cause breakage of the trachea. In all these cases, respiration through the mouth and the nose is no longer possible, or no longer sufficient.

In order to ensure the required degree of gaseous interchange in the lung, an air passage has to be provided by surgical means; this is effected by opening the throat from the outside (tracheotomy) and introducing a respiratory tube (endotracheal tube). However, in many cases of tracheostenosis speaking is no longer or hardly possible after application of an endotracheal tube. In addition, the faculty of smell is also lost since air no loner passes through the nose. Ventral pressure, which is essential for certain functions of the body, and the stabilization of the thorax (for example when lifting heavy objects) are no longer possible as the respiratory air escapes through the endotracheal tube.

In particular the permanent application of an endotracheal tube, which must receive constant care, impairs the quality of life of a patient quite considerably and leads very frequently to considerable psychological stress.

There have been known different approaches for restoring the physiological respiratory tract. But in all these cases, the the chances of success become lower as the lengths of the tracheal segment to be replaced become longer.

There is the possibility, on the one hand, to expand the constricted trachea with the aid of tubular or bolt-like dummies and, on the other hand, to remove cicatricial constrictions with the aid of a laser beam. But experience shows that such forms of treatment are successful only in certain selected cases of tracheostenosis.

If the trachea is damaged only over a short or a moderate length, for example over 2 cm to 4 cm approximately, the affected segment may be resected. The remaining tracheal stumps are then connected by suturing. This method is no longer applicable in the case of long tracheal defects, and is in any case connected with the risk that the vocal cord nerve may be damaged. A method to replace long tracheal segments consists in skin and cartilage grafting. However, these operations often fail because the newly formed respiratory tract is constricted again by the formation of scar tissue and absorption of the grafted cartilage.

In some rare cases, a complete trachea of a cerebrally dead patient has been transplanted. In these cases, there is a great risk of repulsion of the transplant. Likewise, there have been known cases where preserved trachea segments have been transplanted into the trachea of patients suffering from tracheostenosis. In these cases, there is again the risk of repulsion, but also a risk of absorption of the transplant.

In all cases where the before-described methods cannot be employed, where they fail or are rejected by the patient, an artificial trachea suggests itself as a valuable solution.

The use of a tracheal prosthesis enables an existing tracheal defect to be bridged, irrespective of its length, and in addition the respiratory tract, i.e. the lumen of the prosthesis, can be exactly tuned to the patient, according to his age. The tracheostoma can be closed in such a way that physiological breathing is rendered possible through the mouth and the nose. And in addition normal voice production can be achieved in this way.

The difficulties encountered in connection with the application of tracheal prostheses led to the development of special endotracheal tubes, so-called "Montgomery tubes", i.e. a tubular endoprosthesis for constricted tracheal segments which is inserted into the trachea to keep open the air passage. However, a tube connection branching off at an angle of 90° still leads to the outside, through the tracheostoma. This branch is usually closed, but may be opened for cleaning the T-shaped tube or in emergency cases. While such a "Montgomery-T-tube" actually meets higher demands than a simple endotracheal tube, it still requires tracheotomy which constitutes a heavy stress for the patient. In addition, T tubes tend to get occluded by drying mucus, and voice production is also often impaired as part of the breathing air required for speaking escapes through the tracheostoma.

The tracheal prosthesis that has become known consists of a relatively rigid silicon tube the free ends of which taper conically to the outside. In order to embed the implant more securely, the known silicon tube is provided with a plastic ring on both its upper and its lower ends. The known tracheal prosthesis described before has become known under the name "Neville prosthesis".

The "Neville prosthesis" is much less elastic than the human trachea. In addition, the wall of the prosthesis is very rigid and incapable of yielding to the oesophagus which extends closely beside it. Moreover, mucus adhering to the inside of the lumen can be removed only with great difficulty. This may result in occlusion by mucus. The outer surface of the "Neville prosthesis" being very smooth, the prosthesis may also get dislodged in its bedding. As is well known in the art, this has already led to damage to neighboring organs, fistulae between oesophagus and trachea, and to breakage of large neighboring vessels with haemorrhage of a nature dangerous to life. And the known prosthesis is also not in a position to counteract cicatricial constructions on the tracheal stumps.

SUMMARY OF THE INVENTION

Now, it is the object of the present invention to improve the known tracheal prosthesis in such a way as to make its mechanical properties and its shape very much like those of the human trachea.

This object is achieved according to the invention by the fact that the plastic shaft comprises a thin, resilient material wall surrounded by hoops which are spaced one from the other in the axial direction of the plastic shaft and which are connected to the material wall.

This gives the tracheal prosthesis according to the invention the essential advantage that instead of being determined by the material thickness of its plastic shaft, the stability of the prosthesis, similar to that of the human trachea, is determined by the hoops embracing the thin, resilient material wall of the plastic shaft. In combination with the described hoops, the prosthesis according to the invention offers characteristics corresponding substantially to those of the human trachea, as regards extension, bending, compression and torsion. The material of the hoops and the wall are intimately bonded so that any collapse of the prosthesis can be excluded.

If the ends of the hoops are arranged at a certain distance one from the other, they are capable of balancing out pressures exerted on the material wall without thereby impairing the natural stability of the prosthesis.

If the hoops are made from a porous, large-pore plastic material, preferably from polyethylene, a maximum of tissue tolerance is guaranteed. In addition, this plastic material permits the production of porous hoops of an elasticity substantially identical to that of the tracheal cartilage. Further, the tissue in contact with the implant (implant bedding) can grow together with the porous surface structure of the hoops.

If the plastic shaft is made from silicon and is given a wall thickness of 0.3 mm to 1.2 mm, the resulting wall of the prosthesis has the properties of a resilient membrane and is capable of adapting itself very efficiently to the oesophagus resting closely against it.

According to another embodiment of the invention, the hoops are made from a plastic material with a metal insert provided in their core or on their inner surface.

This feature provides the advantage that the hoops can be stabilized additionally.

If, according to another embodiment of the invention, neighboring hoops—viewed in the axial direction—are interconnected by one of their ends so that the hoops form a spiral along the plastic shaft, then the thin, resilient material wall is guided safely and elastically in its longitudinal direction, while the spiral has a stabilizing effect on the material wall with respect to forces acting transversely to the axis of the plastic shaft.

According to a preferred embodiment of the invention, the inner surface of the first lumen is provided with a hydrophilic coating. This makes the inner surface of the lumen wettable so as to provide a durable "pseudo mucus membrane". Given the fact that there always exists a high degree of humidity in the human respiratory tract, it can be assumed that the inner surface of the prosthesis will also be permanently wetted and humid. This improves very considerably the sliding properties of the bronchial mucus so that it can be discharged more easily through the lumen. The hydrophilic coating on the inner surface of the lumen is very similar in its function to the mucus produced by the normal trachea so that very similar motions as in the case of the normal trachea will develop for passive mucus discharge by the breathing function, and by coughing, and this even without cilia.

According to another further development of the invention, a spring element is arranged in the area of the free ends of the material wall. This feature provides the advantage that the end pieces of the prosthesis according to the invention can be connected with the natural tracheal or bronchial stumps safely and durably. This makes the ends of the prosthesis according to the invention particularly resistant to concentrical, cicatricial constriction at the joints between the tracheal or bronchial stumps.

According to another embodiment of the invention, a free end of the plastic shaft terminates by two V-shaped shaft sections comprising each a second and a third lumen and communicating with the first lumen of the plastic shaft. The shaft ends imitate the shape of the bronchial branchings of the human trachea.

The ends of the hoops may be jacketed to provide additional protection against the risk that the ends may get detached from the material wall in an uncontrolled manner. The hoop ends may be provided with a protective cap, or may be welded into or embedded in a reinforced plastic layer.

Other advantages of the invention will appear from the following description and the attached drawing. The features that have been described before and that will be specified hereafter may be employed for the purposes of the invention either individually or in any combination thereof. The embodiments of the invention mentioned above are not to be understood as a comprehensive list of possible applications, but are provided only by way of example.

BRIEF DESCRIPTION OF THE DRAWINGS

The invention will now be described in more detail by way of certain embodiments with reference to the drawing in which.

DETAILED DESCRIPTION

Figure 1:
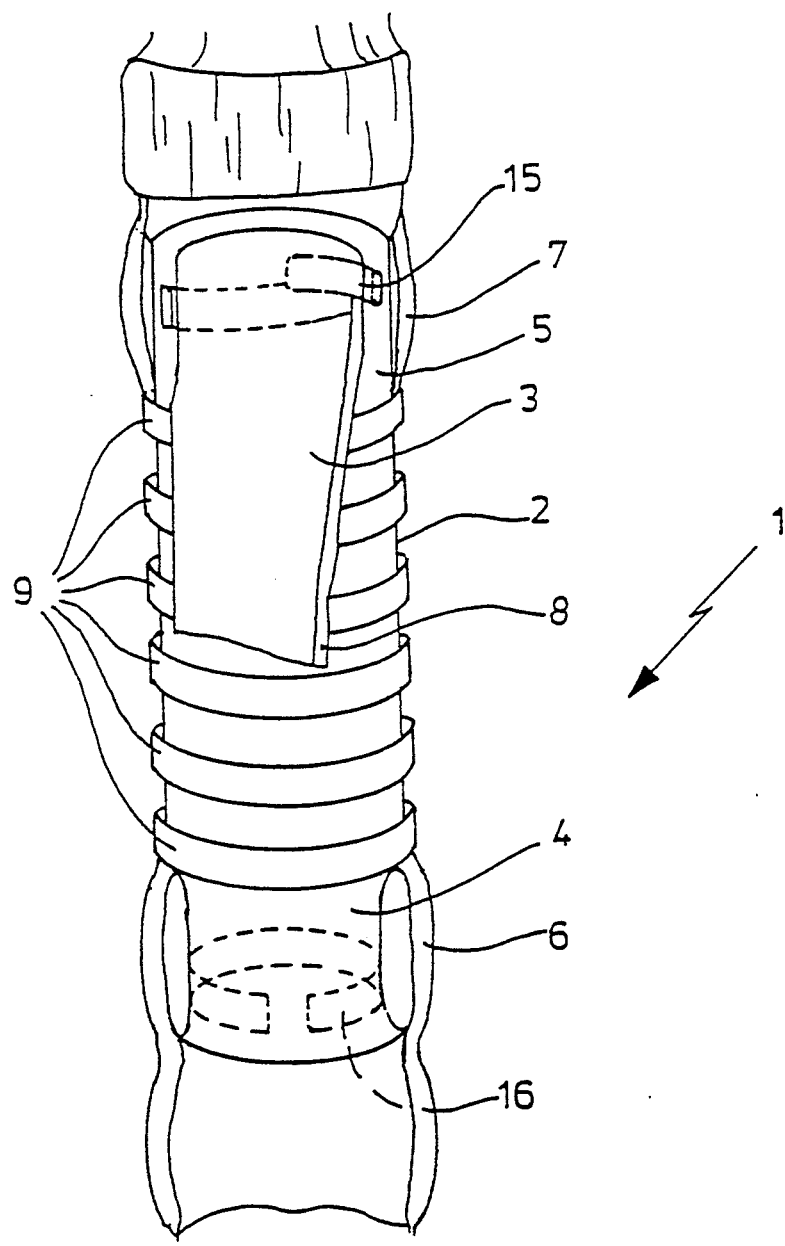
FIG. 1 shows a tracheal prosthesis according to the invention comprising individual hoops, in its position installed in two neighboring tracheal stumps.

The individual figures of the drawing illustrate the object of the invention, partially in a very diagrammatic manner, and not true to scale. The objects of the individual figures are very enlarged in part so that their structure and design can be shown more clearly.

FIG. 1 shows a tracheal prosthesis 1 comprising a plastic shaft 2 with a first lumen 3. The free end 4 and the free end 5 of the plastic shaft 2 are connected with tracheal stumps 6 and 7, respectively. A material wall 8 consisting of a thin-walled plastic film is embraced by hoops 9.

Figure 2:
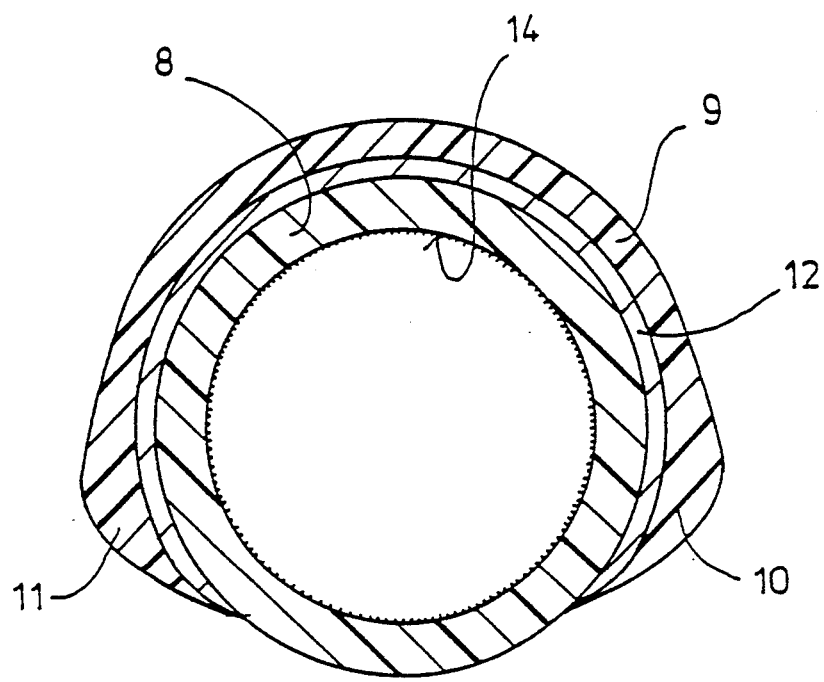
FIG. 2 shows a section through a material wall of a tracheal prosthesis according to the invention, with a hoop embracing the material wall and a metal insert.

FIG. 2 shows ends 10 and 11 of the hoops 9. The hoop 9 according to FIG. 2 is equipped, about its inner circumference, with an insert 12 which is connected directly with the material wall 8. In addition, the insert 12 is connected with the hoop 9 which means that the material wall 8 is connected undetachably with both the hoop 9 and the insert 12.

Figure 3:
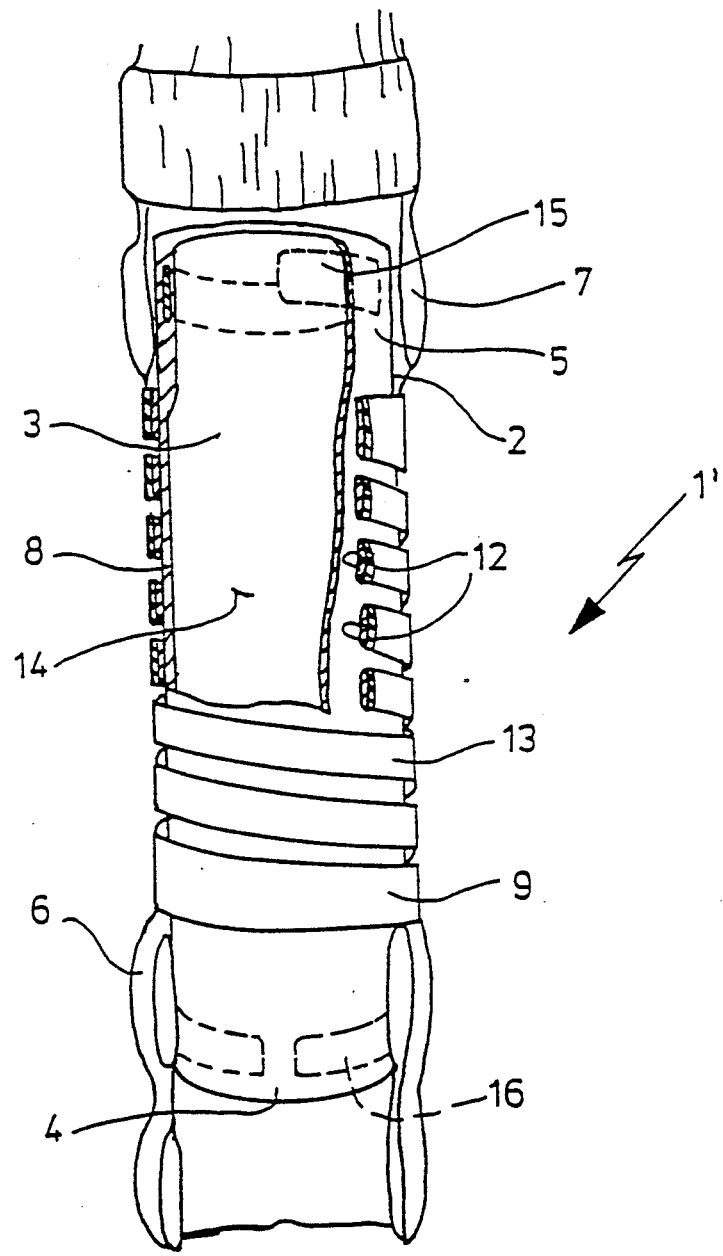
FIG. 3 shows another embodiment of a tracheal prosthesis, with a spiral embracing the material wall.

FIG. 3 shows a tracheal prosthesis 1' of a design corresponding substantially to that of the tracheal prosthesis 1 illustrated in FIG. 1, except that contrary to the arrangement of the tracheal prosthesis 1 according to FIG. 1, the tracheal prosthesis 1' is surrounded by a spiral 13. The spiral 13 may be made from a plastic material and comprises, in the illustrated embodiment, an insert 12 serving to stabilize the spiral 13.

An inner surface 14 of the first lumen 3 provided in both the tracheal prosthesis 1 and the tracheal prosthesis 1' according to FIGS. 1 and 3 is designed as a hydrophilic surface. The inner surface 14 of the lumen 3 is rendered hydrophilic by plasma treatment, plasma polymerization or chemical treatment. FIG. 2 also shows the hydrophilic inner surface 14.

Both the tracheal prosthesis 1 and the tracheal prosthesis 1' are provided with spring elements 15, 16 disposed in the material wall 8, in the terminal area of the prostheses. The free ends 4, 5 of the plastic shaft 2 extend a few millimeters beyond the circumferential surface of the material wall 8 covered by the hoops 9 and/or the spiral 13. The spring elements 15, 16 may serve to reinforce and stabilize the terminal area of the material wall 8.

The material of the wall 8 has a thickness of approx. 0.5 mm increasing to approx. 1 mm towards the ends 4, 5. The hoops 9 have a thickness of 0.5 mm to 2 mm, and axial width of approx. 2 mm to 5 mm. The distance between neighboring hoops 9 is equal to approx. 1 mm to 5 mm. The hoops 9 embrace approx. ⅝ of the circumference of the tracheal prosthesis 1. The inserts 12 embedded in the hoops 2 have a thickness of approx. 0.2 mm and a width of 1.5 to 3 mm. The inserts 12 consist of plastic or metal strips with material characteristics different from those of the hoops 9. The insert 12 may be arranged below the hoop 9, or in its core.

As in the case of the human trachea, the hoops 9 leave certain areas of the plastic shaft 12 uncovered, whereby resilient surface portions are produced between the hoops 9, corresponding to the membranaceous parts of the human trachea. These resilient surface portions establish the contact between the tracheal prosthesis 1, 1' and the oesophagus. The hoops 9 as such exhibit the shape of a ring where one segment has been cut out, or the shape of a horse shoe.

Figure 4:
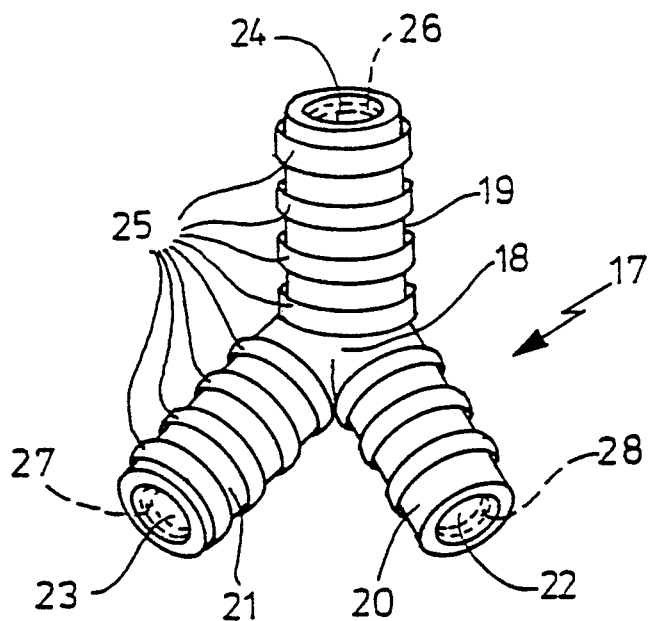
FIG. 4 shows another embodiment of a tracheal prosthesis one end of which imitates bronchial branchings of the human trachea.

FIG. 4 illustrates another embodiment of a tracheal prosthesis 17 according to the invention. The tracheal prosthesis 17 comprises a plastic shaft 19 from which branch sections 20, 21 branch off in V arrangement at the transition 18. The shaft sections 20, 21 comprise a second lumen 22 and a third lumen 23 communicating both with a first lumen 24. The plastic shaft 19 is embraced by hoops 25 the ends of which may be spaced one from the other at the rear of the plastic shaft 19 of the illustrated tracheal prosthesis 17. The broken lines in FIG. 4 indicate spring elements 26, 27, 28 serving to stabilize the ends of the tracheal prosthesis 17. The spring elements 26, 27, 28 give the prosthesis a firm hold in the natural tracheal or bronchial stumps.

Figure 5:
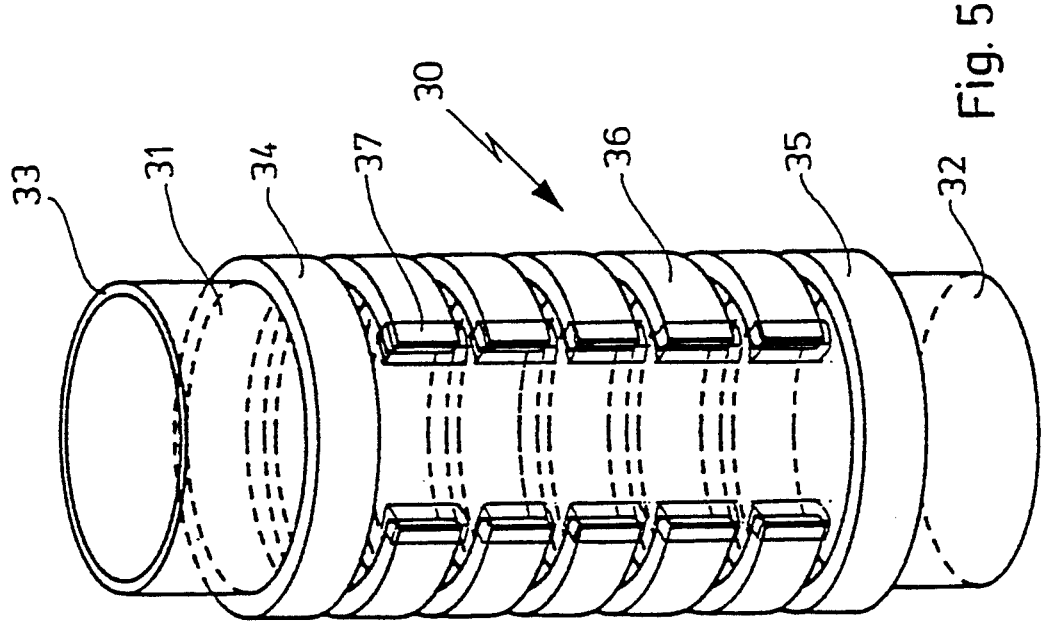
FIG. 5 shows another embodiment of a tracheal prosthesis, with the hoop ends additionally jacketed, viewed from the dorsal end.

FIG. 5 shows an embodiment of a tracheal prosthesis 30 with ends 31, 32 intended to engage matching tracheal stumps. A material wall 33 is surrounded by rings 34, 35 and by hoops 36. The hoops 36 embrace ⅝ of the circumference of the material wall 33 which in its turn has the form of a tube.

The ends of the hoops 36 are provided with a jacket 37 which may take the form of a thicker portion of the material wall 33. The jacket 37 is bonded intimately to the material wall 33.

Figure 6:
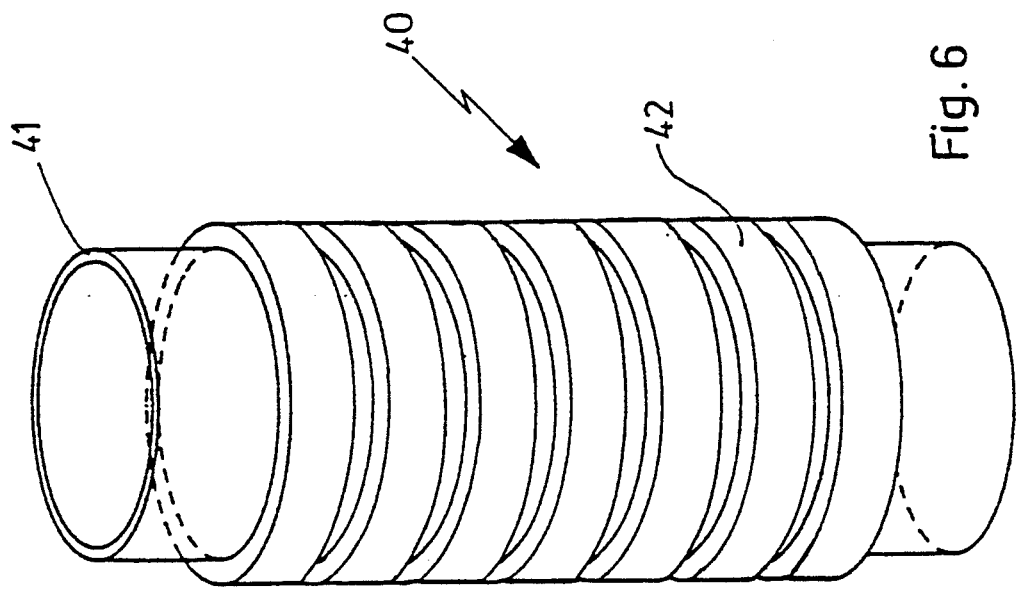
FIG. 6 shows an embodiment of a tracheal prosthesis with annular hoops.

FIG. 6 illustrates a tracheal prosthesis 40 comprising a material wall 41 which is surrounded by annular hoops 42. The annular hoops 42 are provided in spaced relationship one to the other and are connected with the material wall 41.

The tracheal prosthesis 1 serves to replace damaged, diseased or missing tracheal or bronchial segments. The tracheal prosthesis 1 comprises a plastic shaft 2 embraced by hoops 9. The hoops 9 stabilize the thin filmlike material wall 8. As in the case of the human trachea, the hoops 9 leave a certain area of the plastic shaft 2 uncovered whereby a particularly resilient circumferential surface is obtained between the hoops 9, corresponding to the membranaceous part of the human trachea. The ends of the tracheal prosthesis are reinforced by spring elements 15, 16. These spring elements guarantee that the tracheal prosthesis 1 is safely retained in the natural tracheal and/or bronchial stumps 6, 7. The inner surface of the tracheal prosthesis 1 is hydrophilized.

What is claimed is:

1. A tracheal prosthesis shaped and configured to replace natural tracheal and bronchial segments, said tracheal prosthesis comprising:
    a plastic shaft including a lumen and means for joining free ends thereof to tracheal stumps in a person said plastic shaft comprising a thin, resilient material wall surrounded by hoops, said hoops being horseshoe-like shaped and spaced from one another in an axial direction along said plastic shaft and connected to the material wall, said horseshoe-like hoops being non-complete substantially circular collars having tapered ends.

2. The tracheal prosthesis according to claim 1, wherein the hoops are made from a porous, large pore plastic material.

3. The tracheal prosthesis according to claim 1, wherein the plastic shaft is made from silicon and has a wall thickness of 0.3 mm to 1.2 mm.

4. The tracheal prosthesis according to claim 1, wherein the hoops are made from a plastic material with a metal insert disposed in a core thereof.

5. The tracheal prosthesis according to claim 1, wherein an inner surface of the lumen is provided with a hydrophilic coating.

6. The tracheal prosthesis according to claim 1, wherein a spring element is disposed proximate the free ends of the said material wall.

7. The tracheal prosthesis according to claim 1, wherein a free end of the plastic shaft terminates into a V-shaped shaft section comprising a second lumen in a leg of said V-shaped shaft section and a third lumen in another leg of said V-shaped shaft section, said second and third lumens communicating with the lumen of the plastic shaft.

8. The tracheal prosthesis according to claim 1, wherein ends of the hoops are bonded to a jacket.

9. The tracheal prosthesis according to claim 1 wherein the hoops are made from polyethylene.

10. The tracheal prosthesis according to claim 1 wherein the hoops are made from a plastic material with a metal insert disposed on an inner surface thereof.

11. A tracheal shaped and configured to replaces natural prosthesis tracheal and bronchial segments, said tracheal prosthesis comprising:
- a resilient elongate plastic shaft having a lumen defined by an inner surface, said inner surface being coated with a hydrophilic coating;
- means for joining free ends of the shaft with tracheal stumps; and
- hoop means, surrounding said shaft, configured to provide stability to said shaft and enabling the tracheal prosthesis to expand in response to increase in pressure inside the prosthesis and return to an original dimension after expansion, said hoop means comprising a plurality of deformable hoops axially spaced from one another along
- wherein said deformable hoops comprises non-complete substantially circular collars having tapered ends and
- said shaft, said resilient elongate plastic shaft being of sufficient resilience to enable uninhibited expansion of said hoop means.

12. The tracheal prosthesis according to claim 11, wherein the hoops are made of a porous, large-pore plastic material.

13. The tracheal prosthesis according to claim 11, wherein the plastic shaft is made of silicon and has a wall thickness of 0.3 mm to 1.2 mm.

* * * * *